(12) United States Patent
Chen et al.

(10) Patent No.: US 10,316,012 B1
(45) Date of Patent: Jun. 11, 2019

(54) METHOD OF SYNTHESIZING (1S, 5R)-LACTONE

(71) Applicant: FUDAN UNIVERSITY, Shanghai (CN)

(72) Inventors: Fener Chen, Shanghai (CN); Haihui Peng, Shanghai (CN); Sha Hu, Shanghai (CN); Ge Meng, Shanghai (CN); Yan Wu, Shanghai (CN); Dang Cheng, Shanghai (CN); Zedu Huang, Shanghai (CN); Guanfeng Liang, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 0 days.

(21) Appl. No.: 16/246,531

(22) Filed: Jan. 13, 2019

(30) Foreign Application Priority Data

Jan. 15, 2018 (CN) .......................... 2018 1 0033787

(51) Int. Cl.
    *C07D 307/93* (2006.01)

(52) U.S. Cl.
    CPC ................................. *C07D 307/93* (2013.01)

(58) Field of Classification Search
    CPC .................................................... C07D 307/93
    See application file for complete search history.

(56) References Cited

PUBLICATIONS

Xu et al., Eur. J. Org. Chem. 110-116 (2011) (Year: 2011).*

* cited by examiner

*Primary Examiner* — Timothy R Rozof
(74) *Attorney, Agent, or Firm* — Wayne & Ken, LLC; Tony Hom

(57) ABSTRACT

Disclosed is a method of synthesizing a series of compounds with the structure of (1S, 5R)-lactone. In the method, under the catalysis of a chiral phosphonic acid, substituted bicyclo [3.2.0]-hept-2-en-6-one (II) as a substrate is reacted with hydrogen peroxide for enantioselective Baeyer-Villiger oxidation to produce a chiral lactone (I). This method involves mild reaction conditions, simple operation, quantitatively recyclable catalyst and high reaction selectivity and stereoselectivity, which is suitable for industrial production.

7 Claims, No Drawings

METHOD OF SYNTHESIZING (1S, 5R)-LACTONE

CROSS-REFERENCE TO RELATED APPLICATIONS

This application claims the benefit of priority from Chinese Patent Application No. CN201810033787.X, filed on Jan. 15, 2018. The content of the aforementioned application, including any intervening amendments thereto, is incorporated herein by reference in its entirety.

TECHNICAL FIELD

The present application relates to organic chemistry, and specifically to a method of synthesizing a series of compounds with the structure of (1S, 5R)-lactone.

BACKGROUND (1S, 5R)-lactones have the chemical structure shown as the following formula (I):

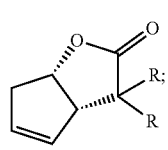

(I)

where R is hydrogen, halogen such as chlorine, bromine and iodine, $C_1$-$C_8$ alkyl or cycloalkyl, phenyl, monosubstituted or polysubstituted aryl or aralkyl, thienyl, furyl or naphthyl.

The (1S, 5R)-lactones of formula (I) are the key intermediates in the synthesis of prostaglandins. The synthesis of (1S,5R)-lactone is first reported by Tolstikov, G. A. et al. (Zhumal Organheskoi Khimii, 1989, 25, 208), where cyclopentadiene is used as a starting material to synthesize a racemic substrate in three steps, and then the racemic substrate is subjected to resolution by diastereomeric crystallization with (R)-(+)-α-methylbenzylamine followed by lactonization to produce the desired (1S,5R)-lactone I. However, these methods involve common resolution problems such as low single-resolution yield, complex operation and high costs. Veronique et al. (Tetrahedron Lett., 1989, 30, 3663) employ bicyclo[3.2.0]-hept-2-en-6-one as a starting material to construct the (1S, 5R)-lactone by one step through microbe-promoted enantioselective Baeyer-Villiger oxidation. Furstoss et al. (J. Org. Chem., 1992, 57, 1306) employ microbe-promoted enantioselective Baeyer-Villiger oxidation to produce the lactone with high enantioselectivity (>95% ee), but there exists undesired lactone products with high enantioselectivity. Moreover, it is difficult to obtain the desired lactone product by separation due to their similar polarities. Masami et al. (Organic Reactions, NJ, United States, 37, Nopp given; 1989) disclose a method for preparing the (1S,5R)-lactone by stereoselective hydrolysis of a meso-diester using pig liver esterase as a catalyst. Ogasawara et al. (Synlett, 1996, 319) reported a method of constructing (1S,5R)-lactone through a lipase-catalyzed desymmetrization reaction. However, these methods are limited to small-scale production, troublesome post-processing, etc. Bolm et al. (Chirality, 2000, 12, 523) first reported in 2000 that asymmetrical Baeyer-Villiger oxidation can be catalyzed by a zirconium-chiral binaphthol catalyst to produce (1S,5R)-lactone with 35% ee. Doyle et al. (Tetrahedron: Asymmetry, 2003, 14, 925) uses a chiral rhodium to catalyze an asymmetric C—H insertion, producing the (1S, 5R)-lactone with 73% yield and 93% ee. Katsuki et al. uses a chiral Zr-Salen catalyst to catalyze the asymmetric Baeyer-Villiger oxidation, producing (1S,5R)-lactone with 23% yield and 91% ee as well as undesired lactones with 38% yield. Ding Kuiling et al. (Eur. J. Org. Chem., 2011, 110) also report that a chiral binaphthyl phosphonic acid is used to catalyze an asymmetric Baeyer-Villiger oxidation to construct the (1S,5R)-lactone with 64% yield and 32% ee. All of the above methods have the disadvantages of expensive catalyst, insufficient catalytic efficiency and low enantioselectivity, thus limiting their industrial application.

SUMMARY

The object of the application is to provide a method of synthesizing a high-purity (1S,5R)-lactone with high yield through the simple operation to overcome the defects in the prior art.

The present invention provides a method of synthesizing (1S,5R)-lactone, comprising:

in the presence of a chiral spirophosphonic acid catalyst, substituted bicyclo[3.2.0]-hept-2-en-6-one (formula II) reacting with a hydrogen peroxide in an organic solvent, under the normal, elevated or reduced pressure for enantioselective Baeyer-Villiger oxidation to produce (1S,5R)-lactone with a total yield of 46% and ee of 95%; wherein the synthetic route is shown as follows:

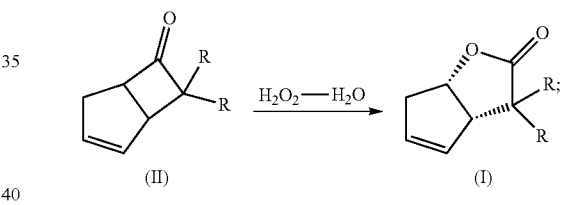

wherein, R is selected from the group consisting of hydrogen, halogen comprising chlorine, bromine and iodine, $C_1$-$C_8$ alkyl or cycloalkyl, phenyl, monosubstituted or polysubstituted aryl or aralkyl, thienyl, furyl and naphthyl.

In the asymmetric ring-opening alcoholysis of the invention, the chiral catalyst is a chiral spirophosphonic acid of formula (A), and this reaction involves high enantioselectively catalytic effect, mild reaction conditions, simple operation, high chemical yield and optical purity and quantitatively recyclable catalyst.

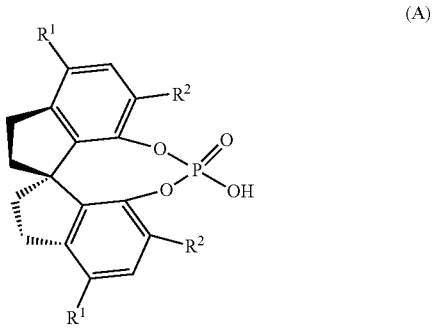

(A)

In formula (A), $R^1$ and $R^2$ are independently selected from the group consisting of hydrogen, halogen comprising chlorine, bromine and iodine, $C_1$-$C_8$alkyl or cycloalkyl, phenyl, monosubstituted or polysubstituted aryl or aralkyl, thienyl, furyl and naphthyl.

In the catalyzed asymmetric Baeyer-Villiger reaction, the hydrogen peroxide is selected from the group consisting of a 10%-80% hydrogen peroxide solution, an adduct of hydrogen peroxide and urea, peroxyacetic acid and m-chloroperoxybenzoic acid. These raw materials are cheap and available from a wide range of sources.

In the catalyzed asymmetric Baeyer-Villiger reaction, the organic solvent is selected from the group consisting of dichloromethane, chloroform, 1,2-dichloroethane, carbon tetrachloride, hexane, heptane, decane, acetonitrile, ethyl acetate, benzene, toluene, xylene, nitrobenzene, diethyl ether, dioxane and tetrahydrofuran. The reaction can be carried out in a single solvent or in a mixture solvent involving solvents mixed at a volume ratio of 1:0.1-10. These solvents are available from a wide range of sources, which are cheap and easy to recycle.

In the catalyzed asymmetric Baeyer-Villiger reaction, the chiral catalyst is preferably (11aR)-10,11,12,13-tetrahydro-5-hydroxy-3,7-bis[2,4,6-triisopropyl-phenyl]-5-oxide-diindeno[7,1-de:1',7'-fg][1,3,2]dioxaphosphocin. The chiral catalysts are simple to prepare and recycle and are cost-effective.

In the catalyzed asymmetric Baeyer-Villiger reaction, the hydrogen peroxide is preferably a 10%-80% hydrogen peroxide solution.

In the catalyzed asymmetric Baeyer-Villiger reaction, a molar ratio of cyclobutanone to hydrogen peroxide to chiral catalyst is 1:1-5:0.05-1, preferably 1:1-5:0.05-0.5. The reaction is successfully completed.

In the catalyzed asymmetric Baeyer-Villiger reaction, a reaction temperature is −40-25° C., preferably 20-0° C., allowing for simple industrial production of lactone.

In the catalyzed asymmetric Baeyer-Villiger reaction, a reaction time is 24-72 hours, preferably 36-72 hours.

In the catalyzed asymmetric Baeyer-Villiger reaction, the solvent is most preferably chloroform, which are available from wide range of sources and easy to recycle.

The invention is suitable for large-scale production owing to the advantages of available raw materials, mild reaction conditions, simple operation, high chemical yield and optical purity, recyclable catalyst and low cost.

DETAILED DESCRIPTION OF EMBODIMENTS

The invention will be further described below with reference to embodiments, but the invention is not limited to these embodiments.

Example 1

7,7-Dichlorobicyclo[3.2.0]-hept-2-en-6-one (1.77 g, 0.01 mol), (11aR)-10,11,12,13-tetrahydro-5-hydroxy-3,7-bis[2,4,6-triisopropyl-phenyl]-5-oxide-diindeno[7,1-de:1',7'-fg][1,3,2]dioxaphosphocin (0.35 g, 0.005 mmol), hydrogen peroxide solution (30%, 2.5 mL, 0.03 mol) and chloroform (20 mL) were added to a dry reaction flask and stirred at −20-0° C. for 36-72 hours. After the reaction was completed, the solvent was recycled under vacuum, and the residue was added with diethyl ether (50 mL) and stirred for 15 minutes after the residue was cooled to room temperature. Hydrochloric acid (10%, 50 mL) was added and stirred for 30 minutes followed by standing to form an organic layer. The organic layer was separated, dried with anhydrous sodium sulfate, and filtered to produce a filtrate. The filtrate was processed under vacuum to recycle the solvent and to produce a solid product. The solid product was dried to obtain a white powder, which was recrystallized from diethyl ether to obtain product II (R=Cl, 46% yield, 96.9% ee).

$^1$HNMR (CDCl$_3$): 5.99 (s, 1H), 5.74 (s, 1H), 5.28 (s, 1H), 4.10 (s, 1H), 2.81 (s, 2H).

Example 2

7,7-Dichlorobicyclo[3.2.0]-hept-2-en-6-one (1.77 g, 0.01 mol), (11aR)-10,11,12,13-tetrahydro-5-hydroxy-3,7-bis[2,4,6-triisopropyl-phenyl]-5-oxide-diindeno[7,1-de:1',7'-fg][1,3,2]dioxaphosphocin (0.35 g, 0.005 mmol), hydrogen peroxide solution (30%, 2.5 mL, 0.03 mmol) and chloroform (20 mL) were added to a dry reaction flask, and stirred at −40° C. to −20° C. for 48-72 hours. After the reaction was completed, the solvent was recycled under vacuum, and the residue was added with diethyl ether (50 mL) and stirred for 15 minutes after the residue was cooled to room temperature. Hydrochloric acid (10%, 50 mL) was added and stirred for 30 minutes followed by standing to form an organic layer. The organic layer was separated, dried with anhydrous sodium sulfate and filtered to produce a filtrate. The filtrate was processed under vacuum to recycle the solvent and to produce a solid product. The solid product was dried to obtain a white powder, which was recrystallized from diethyl ether to obtain product II (R=Cl, 46% yield, 96.9% ee).

$^1$HNMR (CDCl$_3$): 5.99 (s, 1H), 5.74 (s, 1H), 5.28 (s, 1H), 4.10 (s, 1H), 2.81 (s, 2H).

Example 3

7,7-Dichlorobicyclo[3.2.0]-hept-2-en-6-one (1.77 g, 0.01 mol), (11aR)-10,11,12,13-tetrahydro-5-hydroxy-3,7-bis[2,4,6-triisopropyl-phenyl]-5-oxide-diindeno[7,1-de:1',7'-fg][1,3,2]dioxaphosphocin (0.35 g, 0.005 mmol), hydrogen peroxide solution (30%, 2.5 mL, 0.03 mmol) and chloroform (20 mL) were added to a dry reaction flask, and stirred at −20° C. to 20° C. for 36-72 hours. After the reaction was completed, the solvent was recycled under vacuum, and the residue was added with diethyl ether (50 mL) and stirred for 15 minutes after the residue was cooled to room temperature. Hydrochloric acid (10%, 50 mL) was added and stirred for 30 minutes followed by standing to form an organic layer. The organic layer was separated, dried with anhydrous sodium sulfate, and filtered to produce a filtrate. The filtrate was processed under vacuum to recycle the solvent and to produce a solid product. The solid product was dried to obtain a white powder, which was recrystallized from diethyl ether to obtain product II (R=Cl, 46% yield, 96.9% ee).

$^1$HNMR (CDCl$_3$): 5.99 (s, 1H), 5.74 (s, 1H), 5.28 (s, 1H), 4.10 (s, 1H), 2.81 (s, 2H).

What is claimed is:
1. A method of synthesizing a (1S,5R)-lactone of formula (I), comprising:

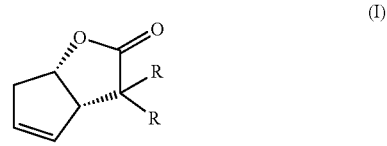

(I)

in the presence of a chiral phosphonic acid catalyst, substituted bicyclo[3.2.0]-hept-2-en-6-one reacting with a hydrogen peroxide in an organic solvent under normal, elevated or reduced pressure for enantioselective Baeyer-Villiger oxidation to produce a chiral lactone; where the substituted bicyclo[3.2.0]-hept-2-en-6-one is presented by structural formula (II)

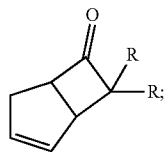
(II)

wherein:
in formula (I), R is selected from the group consisting of hydrogen, halogen comprising chlorine, bromine and iodine, $C_1$-$C_8$alkyl or cycloalkyl, phenyl, monosubstituted or polysubstituted aryl or aralkyl, thienyl, furyl and naphthyl;
in formula (II), R is selected from the group consisting of hydrogen, halogen comprising chlorine, bromine and iodine, $C_1$-$C_8$alkyl or cycloalkyl, phenyl, monosubstituted or polysubstituted aryl or aralkyl, thienyl, furyl and naphthyl;
the chiral phosphonic acid catalyst is an (11aR)-spiro-phosphonic acid of formula (A):

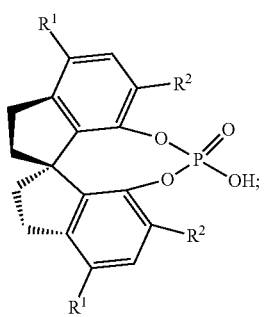
(A)

wherein, $R^1$ and $R^2$ are selected independently from the group consisting of hydrogen, halogen comprising chlorine, bromine and iodine, $C_1$-$C_8$alkyl or cycloalkyl, phenyl, monosubstituted or polysubstituted aryl or aralkyl, thienyl, furyl and naphthyl;

hydrogen peroxide is selected from a 10%-80% hydrogen peroxide solution, an adduct of hydrogen peroxide and urea, peroxyacetic acid or m-chloroperoxybenzoic acid;

a molar ratio of cyclobutanone to hydrogen peroxide to chiral catalyst is 1:1-10:0.05-1.1;

the organic solvent is a single solvent or mixture solvent;

a reaction temperature is −80-25° C.; and a reaction time is 10-80 hours.

2. The method of claim 1, wherein the chiral phosphonic acid catalyst is (11aR)-10,11,12,13-tetrahydro-5-hydroxy-3,7-bis[2,4,6-triisopropyl-phenyl]-5-oxide-diindeno[7,1-de:1',7'-fg][1,3,2]dioxaphosphocin.

3. The method of claim 1, wherein the hydrogen peroxide is a 10%-80% hydrogen peroxide solution.

4. The method of claim 1, wherein the molar ratio of cyclobutanone and the hydrogen peroxide and the chiral catalyst is 1:1-5:0.05-1.

5. The method of claim 1, wherein the organic solvent is selected from the group consisting of dichloromethane, chloroform, 1,2-dichloroethane, carbon tetrachloride, hexane, heptane, decane, acetonitrile, ethyl acetate, benzene, toluene, xylene, nitrobenzene, diethyl ether, dioxane and tetrahydrofuran.

6. The method of claim 1, wherein the reaction temperature is −40-25° C.

7. The method of claim 1, wherein the reaction time is 24-72 hours.

* * * * *